US 6,604,259 B2

(12) United States Patent  
Shofner et al.

(10) Patent No.: US 6,604,259 B2  
(45) Date of Patent: Aug. 12, 2003

(54) ULTRA RAPID CONDITIONING OF COTTON FIBER FOR TESTING AND PROCESSING

(75) Inventors: Frederick M. Shofner, Knoxville, TN (US); Christopher K. Shofner, Knoxville, TN (US)

(73) Assignee: Shofner Engineering Associates, Inc., Knoxville, TN (US)

( * ) Notice: Subject to any disclaimer, the term of this patent is extended or adjusted under 35 U.S.C. 154(b) by 0 days.

(21) Appl. No.: 10/155,822

(22) Filed: May 24, 2002

(65) Prior Publication Data

US 2002/0178547 A1 Dec. 5, 2002

Related U.S. Application Data

(62) Division of application No. 09/663,497, filed on Sep. 15, 2000, now Pat. No. 6,397,437.
(60) Provisional application No. 60/221,104, filed on Jul. 27, 2000, provisional application No. 60/182,731, filed on Feb. 15, 2000, and provisional application No. 60/154,527, filed on Sep. 16, 1999.

(51) Int. Cl.⁷ .................................................. D01B 3/04
(52) U.S. Cl. .................................. 19/66 CC; 19/66 R
(58) Field of Search ............................ 19/66 CC, 48 R, 19/39, 40, 64.5, 66 R; 73/159, 160, 865.6; 700/130, 139, 140, 142, 143, 144

(56) References Cited

U.S. PATENT DOCUMENTS

| 2,834,058 A | * | 5/1958 | Bryant ..................... 19/66 CC |
| 3,247,552 A | * | 4/1966 | Bryant et al. ............. 19/66 CC |
| 3,324,513 A | | 6/1967 | Hurdt ....................... 19/66 CC |
| 3,335,465 A | | 8/1967 | Fahringer ................. 19/66 CC |
| 3,357,061 A | | 12/1967 | Jackson .................... 19/66 CC |
| 3,451,105 A | * | 6/1969 | Nayfa ....................... 19/66 CC |
| 4,512,060 A | | 4/1985 | Shofner ........................ 19/200 |
| 4,631,781 A | | 12/1986 | Shofner ........................ 19/200 |
| 4,667,373 A | * | 5/1987 | Roder ......................... 19/66 R |
| 4,686,744 A | | 8/1987 | Shofner ......................... 19/105 |
| 4,943,300 A | | 7/1990 | Vinnikov ....................... 19/66 R |

(List continued on next page.)

FOREIGN PATENT DOCUMENTS

| WO | WO 01/20321 A2 | 3/2001 |
| WO | WO 01/20321 A3 | 3/2001 |

OTHER PUBLICATIONS

J.L. Knowlton and Roger K. Alldredge, "Experience with Rapid Conditioning of HVI Samples," Beltwide Cotton Conference, San Diego, California, Jan. 1994.

Darryl W. Earnest, "Advancements in USDA Cotton Classing Facilities," Engineered Fiber Conference, Raleigh, North Carolina, May 1966.

Michael D. Watson, Robert S. Baird and Frederick M. Shofner, "Australian and American Experience with Rapid-Con ™," presented at the Beltwide Cotton Conferences, New Orleans, Louisiana, Jan. 9, 1997.

*Primary Examiner*—Gary L Welch  
(74) *Attorney, Agent, or Firm*—Carter Schnedler & Monteith, P.A.

(57) ABSTRACT

Machine for ultra-rapidly condition cotton fiber. In a processing embodiment for conditioning fiber being pneumatically transported by a gas flow, fibers are collected to form a thin mat. Aerosolized liquid is delivered to the thin mat, and then conditioned fiber form the thin mat is re-delivered into the gas flow.

38 Claims, 7 Drawing Sheets

U.S. PATENT DOCUMENTS

| | | | |
|---|---|---|---|
| 5,121,522 A | 6/1992 | Leifeld et al. | 19/66 CC |
| 5,361,450 A | 11/1994 | Shofner et al. | 19/66 CC |
| 5,381,587 A * | 1/1995 | Vandergriff | 19/48 R |
| 5,537,868 A | 7/1996 | Shofner et al. | 73/160 |
| 5,560,194 A | 10/1996 | Shofner et al. | 57/264 |
| 5,676,177 A | 10/1997 | Shofner et al. | 139/1 |
| 5,890,264 A * | 4/1999 | Shofner et al. | 19/205 |
| 5,910,598 A | 6/1999 | Shofner et al. | 139/1 |
| 5,929,460 A * | 7/1999 | Shofner et al. | 250/574 |
| 6,029,316 A | 2/2000 | Shofner et al. | 19/66 |
| 6,314,618 B1 * | 11/2001 | Mehner et al. | 19/48 R |
| 6,397,437 B1 * | 6/2002 | Shofner et al. | 19/66 C |

* cited by examiner

ULTRA RAPID CONDITIONING OF COTTON FIBER FOR TESTING AND PROCESSING

CROSS-REFERENCE TO RELATED PATENT APPLICATIONS

This is a division of U.S. patent application Ser. No. 09/663,497, filed Sep. 15, 2000 now U.S. Pat. No. 6,397,437. The benefit of U.S. Provisional Patent Application Ser. No. 60/154,527, filed Sep. 16, 1999; Ser. No. 60/182,731, filed Feb. 15, 2000; and Ser. No. 60/221,104, filed Jul. 27, 2000 is claimed.

BACKGROUND OF THE INVENTION

The invention relates generally to fiber quality measurements for cotton classing, more particularly, to conditioning samples of cotton fiber prior to instrument testing and to conditioning in-process cotton for optimal processing in gins or mills.

Cotton standards are supported by the United States Department of Agriculture (USDA) through its Agricultural Marketing Service (AMS). Cotton standards, and the corresponding classing of cotton, are of great importance in determining the market value of a particular bale of cotton, as well as determining suitability of a particular bale of cotton from a gin for subsequent processing at a particular mill in view of the products and processes of that mill. AMS is responsible for preparing and maintaining such cotton standards and does so in its Standards Section located in Memphis, Tenn.

In 1923, the United States and nine European countries entered into the Universal Cotton Standards Agreement. From that time, up until approximately 1965, USDA/AMS cotton classing "measurements" based on the Universal Standards were made entirely by humans. The human measurements included "grade," "extraneous matter" (such as bark and grass), "preparation" (which relates to smoothness of the sample) and "staple length" (long fiber content). Instrument-based cotton classing was introduced in 1965, beginning with micronaire, followed in 1980 by High Volume Instruments (HVI), which added measurements of length and strength. HVIs currently measure the fiber qualities of Micronaire, Length, Strength, Color and Trash. Some of those fiber quality measurements, notably strength and length are strongly affected by the fiber moisture content. Some proposed additional measurements, notably stickiness, nep content and cleanability, are also strongly affected by moisture content. It follows that it is very important to assure correct moisture content for fiber quality testing. Historically, this has meant allowing 72 hours equilibration time. More recently, rapid conditioning, as described below, can reduce these equilibration times to about 15 minutes. But in many cases, equilibration times of seconds are needed.

Similarly, optimal processing of cotton fiber is strongly affected by moisture content of the material. Gin and mill processing applications demand conditioning times, that is, times to approach equilibria of various processing performance parameters that are seconds, not minutes.

Accordingly, both testing and processing applications require conditioning times that are much shorter than known. Equally or more importantly, the equilibria reached throughout the sample or process materials must be uniform.

Major factors in sample preparation are the precision and accuracies of environmental conditions in which these steps take place. It is also well known that environmental conditions in the testing zones of materials property testing laboratories or instruments can strongly affect test results. This fact is generally important for fiber testing, and particularly critical for cotton, and other natural fibers, and for rayon, and other man-made fibers.

Prior to more recent developments in "rapid conditioning," for more than seventy-five years, certain fiber, yarn, or fabric tests have been conducted under so-called "Standard Laboratory Environment" or ASTM conditions of 65% relative humidity and 70° F. (21° C.) dry bulb temperature. Since what matters most, for good test results, is not conditions in the lab but conditions in the samples (and within the testing zones) at the time of testing, the various ASTM methods for fiber, yarn, or fabric samples further include the requirement that the samples to be tested be stored or "conditioned" in the standard environment for 72 hours prior to testing in the standard environment. This storage time presumably allows the samples to "reach equilibrium." It is noted that samples so conditioned are passively equilibrating, and that equilibrium usually refers to sample moisture content. Moisture content is the weight of water in the sample as a percentage of the dry weight of the sample. For cotton, equilibrium moisture content MC is about 7.3% at 65% RH, 70° F. (21° C.).

It should however be noted that moisture content is only one fiber, yarn, or fabric material property measurement whose equilibrium value is of interest. Others include tenacity, length, stickiness and neps, and such fiber properties are much more important for selling, buying and using the fibers than is moisture content. We note that moisture content affects other fiber material properties, and is therefore a very important control variable, but is not as important for marketing or processing purposes.

Whereas equilibration times of 72 hours historically yield consistent test results, such periods are unacceptably long in today's intensely competitive and information-hungry marketplace. It is therefore critically important that the tests be executed accurately and precisely, that is, with minimal bias or random errors. But testing before equilibria in the tested properties are reached can disastrously (in profit/loss terms) reduce accuracy and precision. (Equilibrium times are different for different materials test parameters.)

Similar and sometimes more severe constraints apply to optimal process controls. Since fiber processing parameters very strongly depend upon the equilibrium fiber qualities, it is important to control said equilibrium values very rapidly, and also very uniformly.

Recognizing the severe conflict between promptly available results versus good (precise and accurate) results, the United States Department of Agriculture Agricultural Marketing Service, Cotton Division, began investigations in the early 1990's into actively and rapidly conditioning cotton samples. These investigations were remarkably successful and proved that well-conditioned laboratory air could be actively drawn through HVI samples (as opposed to passive or diffusional mass and heat transfer), which active conditioning or "rapid conditioning" enabled samples to reach moisture content or strength equilibrium in less than about 15 minutes.

Various United States Department of Agriculture papers describe "rapid conditioning." Examples are J. L. Knowlton and Roger K. Alldredge, "Experience with Rapid Conditioning of HVI Samples," Beltwide Cotton Conference, San Diego, Calif., January 1994; and Darryl W. Earnest, "Advancements in USDA Cotton Classing Facilities," Engineered Fiber Conference, Raleigh, N. C., May 1996. "Rapid conditioning" is now employed in most of the fourteen USDA/AMS cotton classing offices.

In our earlier efforts to extend USDA rapid conditioning results to small instrument classing operations having one to four HVIs (versus twenty to forty), and not having well-conditioned laboratories, it was discovered that simply drawing 65%, 70° F. (21° C.) air through the samples for 15 minutes yielded unacceptable test results for very dry and wet samples, and that unacceptably long conditioning times were required to achieve good results. It was also found that sample type (i.e., variety) and size and bulk density affected test results and conditioning times.

More recently, and addressing the concerns noted just above, Shofner et al U.S. Pat. No. 6,029,316 discloses methods and a machine for "rapidly" conditioning samples of cotton fiber prior to testing. Twenty-four cotton classing samples, each weighing about 0.25 to 0.75 pounds (113 to 340 grams) are placed within a sample tray having a perforated bottom. The machine includes a sensor for measuring sample moisture content, and a controller for determining a sample specific conditioning cycle based on measured moisture content. The determined conditioning cycle is one which causes the samples to be conditioned to an optimum state for testing. Gas flow conditioning apparatus effects the conditioning cycle by driving a conditioned gas flow through the samples. Key features of such forced ventilation flows through the material are flow velocities of about 100 feet/min and sample specific conditioning cycles having variable temperatures F and relative humidities RH.

In the context of that invention, "rapidly" means conditioning a sample within about 15 minutes but much more uniformly and, also more generally, as very dry, wet or large samples can be conditioned employing embodiments of the invention.

SUMMARY OF THE INVENTION

Embodiments of the invention condition samples of cotton for satisfactory testing (or processing) in a matter of seconds, and do not require conditioned laboratory or processing facility space, as the conditioning is accomplished internally to the testing instrument or processing machine. Key features of the invention are high velocity gas flows through thin mats of material and delivery of moisture and other chemicals in both gaseous and aerosol forms. Important operational features are total moisture concentration (grams of gaseous and aerosolized water per cubic meter of gas, typically air), precisely controlled aerosol particle size distribution, the balance between aerosolized and gaseous water, and the composition and quantities of other chemicals delivered with the water.

DETAILED DESCRIPTION

Figure 1:
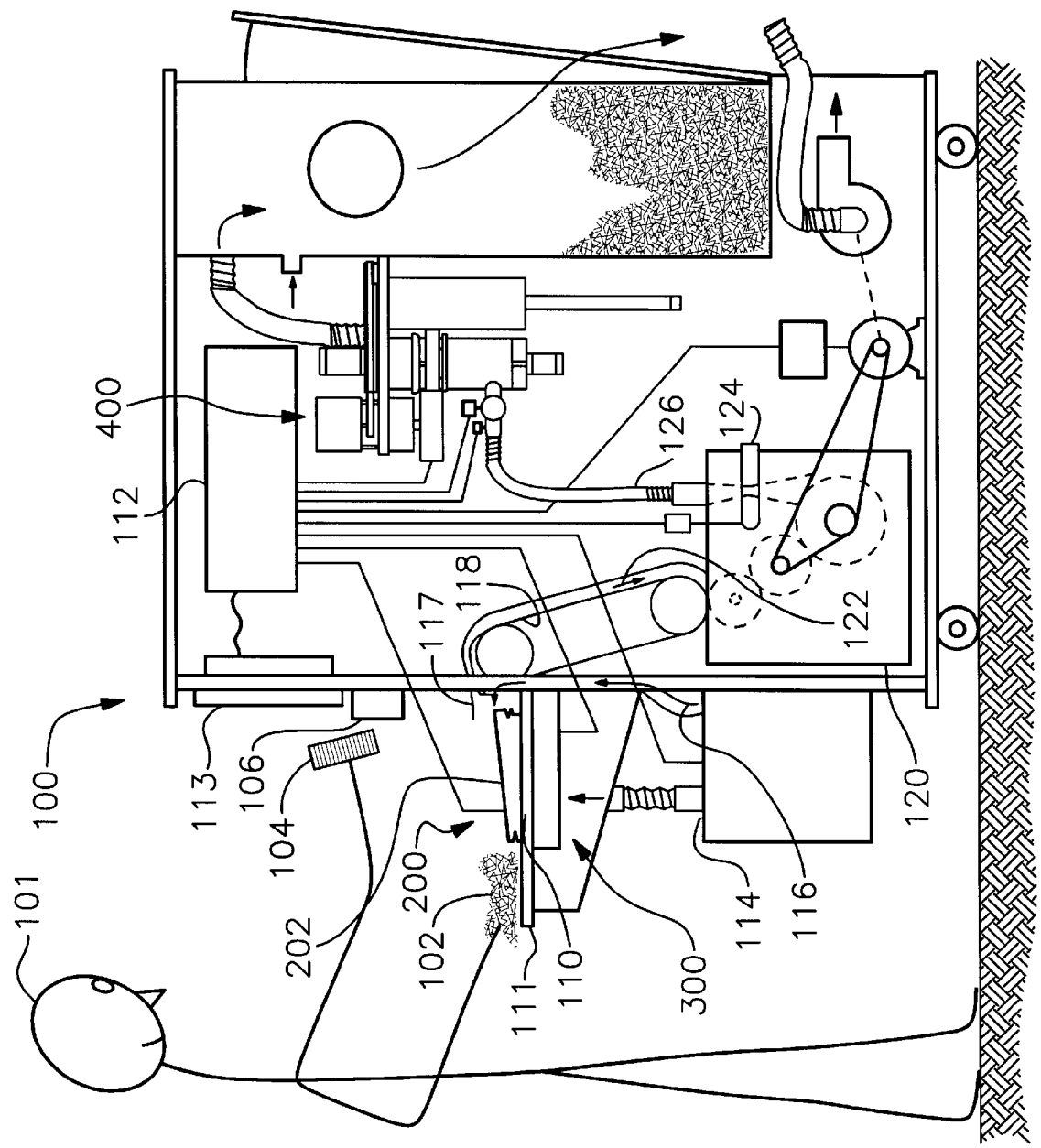
FIG. 1 is an overview of a machine embodying the invention, which machine measures cotton samples to produce multiple data products, including images, and additionally internally and ultra-rapidly conditions samples.

Referring first to FIG. 1, the invention is embodied in a stand-alone instrument 100 which measures fiber qualities 30 of cotton samples to produce multiple data products, including images, and additionally internally and ultra-rapidly conditions the samples. Instrument 100 is a robust, stand-alone alone platform, upon which multiple fiber quality measurement modules are placed, and is generally described in the invited paper F. M. Shofner and C. K. Shofner "Cotton Classing in the New Millennium," 25th International Cotton Conference, Bremen, Germany, Mar. 1–4 2000. By including internal, ultra-rapid sample conditioning, the instrument 100 enables rapid testing and eliminates the need for expensive conditioned laboratory space. The instrument 100, known as "RapidTester," thus does the work of several other instruments and an expensive laboratory air conditioning system, and does that work in the challenging ginning environment as well as in laboratories.

In a fiber testing embodiment, a thin test specimen, about 15 grams, is spread over an impervious plate having linear dimensions of about 8.5×8.5 inches (21.59×21.59 cm). The plate may be glass, through which optical measurements are made. The sample may be compressed for optical testing purposes by a perforated plate with a pressure in the range of about 0.1 to 1 pound force per square inch ($6.895 \times 10^3$ to $6.895 \times 10^4$ dyne/cm$^2$), but a wide range of pressures are useful. When so compressed, the sample thickness is about 0.06 inch (1.5 mm). Conditioning air is driven into entry holes in the perforated plate, moves transversely through the testing sample between the perforated and solid plates, and then moves out of adjacent exit holes of the perforated plate. For testing purposes, the conditioning air may deliver only gaseous and aerosolized water, no chemicals, and the deliveries may be constant or variable, depending on the entering sample conditions and the testing objectives.

System Overview

Operator 101 in FIG. 1 selects a "Classer's Sample," or sub-sample thereof, having an estimated weight of approximately 15 grams of sample 102. Such a 15-gram sample is typically 5 inches (12.7 cm) wide×8 inches (20.32 cm) long×0.5 inch (1.27 cm) thick, when uncompressed. The operator "swipes" permanent bale identification (PBI) tag 104 through bar code reader 106, and prepares and introduces sample 102 into recessed conditioning/test chamber 110 of "stable table" top 111, when pressure/distribution plate 202 is retracted. (See also FIG. 2.) The operator 101 then initiates automatic conditioning/testing by causing pressure/distribution plate 202 to move over sample 102 in the recessed conditioning/testing chamber 110, compressing the sample to a thickness of less than 3 mm. Directed by a process control computer 112, the instrument 100 then automatically effects "Ultra-Rapid Conditioning" in module 200, and additionally effects testing of the sample 102 for Color and Trash in module 300. (Operator 101 can monitor and control the progress of conditioning/testing, and of all other operations, as well as examine the data products produced, stored, and communicated by system 100 via computer 112 and touch-screen display 113.)

Conditioned gas for conditioning sample 102 in conditioning/testing chamber 110 and for transporting and processing sample 102 in subsequent steps is provided by air conditioning module 114. Air conditioning module 114 provides a conditioned gas flow 116 having controlled environmental parameters such as Relative Humidity of 65%, dry bulb Temperature of 70° F. (21° C.), flow rates of 200 CFM (5.7 m$^3$/min). Conditioned gas flow 116 is conducted to the entrance 117 for both the individualizer 120 (flow 122) and for the sample conditioning module 200. In a variation, gas flow 116 is split into two components, one having the fixed, standard parameters just described and a second having variable humidity, temperature, flow rate and pressure and which variable parameters are automatically controlled by a separate controller within air conditioner 114, and which parameter values are determined in accordance with optimally conditioning sample 102 within conditioning/testing chamber 110. Either flow may contain aerosolized water and chemicals, as explained hereinbelow.

In overview, sample 102, having been manually or automatically placed in recessed conditioning/testing chamber 110, with the pressure/distribution plate assembly 202 over it, is ultra-rapidly "conditioned" from above window 204 and "tested" for Color and Trash below it. Sample 102 may also be tested for moisture content in chamber 110, according to which data air conditioning module 114 is caused to optimally condition sample 102 under control of computer 112.

As a practical matter, the nominal transverse dimensions of the conditioning module 200 and Color and Trash testing module 300 are 8.5×8.5 inches (21.59×21.59 cm), the width being related to the width of standard paper in the United States. This is because the Color and Trash module 300 is based on available high quality and high resolution color scanners intended for office and graphics arts use in scanning documents. However, any transverse dimensions may be employed.

The substantially simultaneous Ultra-Rapid Conditioning by module 200 and image acquisition testing by module 300 lasts less than one minute and can be as short as ,approximately ten seconds, depending on scanner resolution chosen and how close in moisture content the selected sample 102 lies to an acceptable value, such as 7.3% for cotton.

At the completion of the conditioning/testing cycle, cover 202 is opened. The cover may be opened manually, or automatically upon receipt of a signal from computer 112. Sample 102, which is now conditioned for further processing and testing, is automatically or manually moved onto belt 118 for quick transport to an individualizer 120, which thoroughly opens, i.e., "individualizes," sample 102 into its various constituent entities, fibers, neps, trash, seed coat fragments, sticky points, microdust, and the like. A suitable individualizer is disclosed in Shofner et al U.S. Pat. No. 5,890,264. An alternative is for individualizer 120 to also clean sample 102 by removing trash, microdust and other foreign matter. However, in the disclosed embodiment almost all of the individualized entities are transported in the same transport flow stream.

This processing by individualizer 120 causes the thoroughly individualized entities to be entrained in or transported by about 120 CFM (3.4 m$^3$/min) of conditioned air flow 122 such that the fiber and other entity concentrations transported by the gas flow at the output 126 of individualizer 120 are very low. Accordingly, the Nep content of thus-individualized sample 102 is measured with a nep sensor 124 which advantageously is built into the individualizer 120. A suitable nep sensor 124 is as disclosed in Shofner et al U.S. Pat. No. 5,929,460.

Sample 102, whose weight was guessed by operator 101 at approximately 15 grams, is at the output 126 of individualizer 120 in a highly opened, individualized state that simulates the state of fiber in important textile processing machines, especially carding. Accordingly, the state of the fiber is ideal for testing the individual fibers and other entities in the gas flow 122. One such test is the Nep test made by nep sensor 124. Other tests are Micronaire-Maturity-Fineness (MMF), effected by module 400. For Neps and for MMF, it is required that the sample weight be known, not guessed, and sample masses of nominally ten grams are commonly used for both tests.

The system aspects of the disclosed embodiment can be summarized:

1. Common flow;
2. Optimal sequence for sample tests, from surface measurements of Color and Trash to volume or weight measurements of Neps and Micronaire based on guessed weight or on precise weight;
3. Ideal sample state for simulations of actual processing (e.g., cleanability, processability, spinnability); and
4. Automatic except for selecting and introducing classer's sample, thus eliminating operator effort and errors. System and methods can be extended to complete automation.

Ultra Rapid Conditioning

Figure 2:
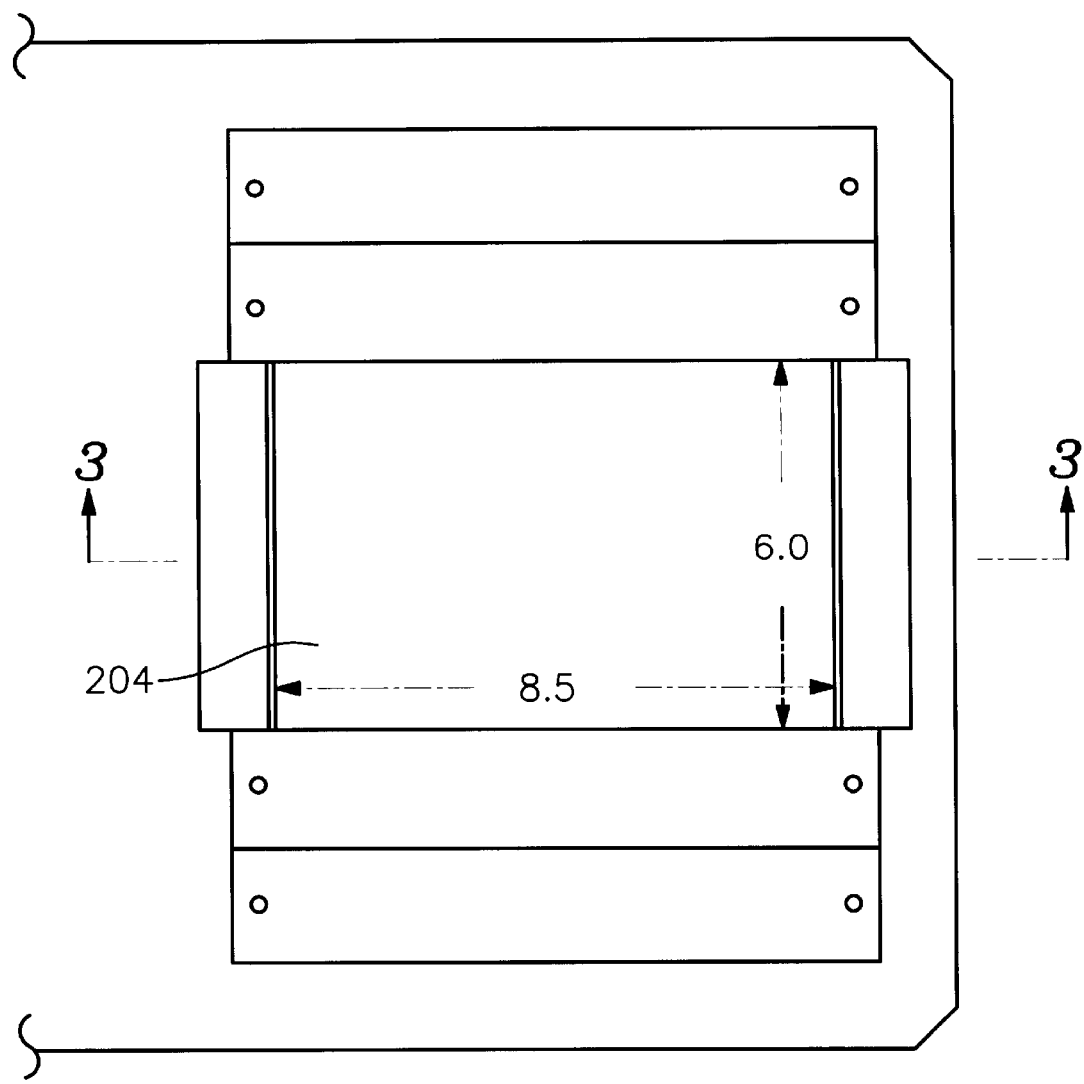
FIG. 2 is a top view of the Ultra-Rapid Conditioning module and the Color and Trash module of the machine of FIG. 1, without a pressure/distribution cover plate in place.
Figure 3:
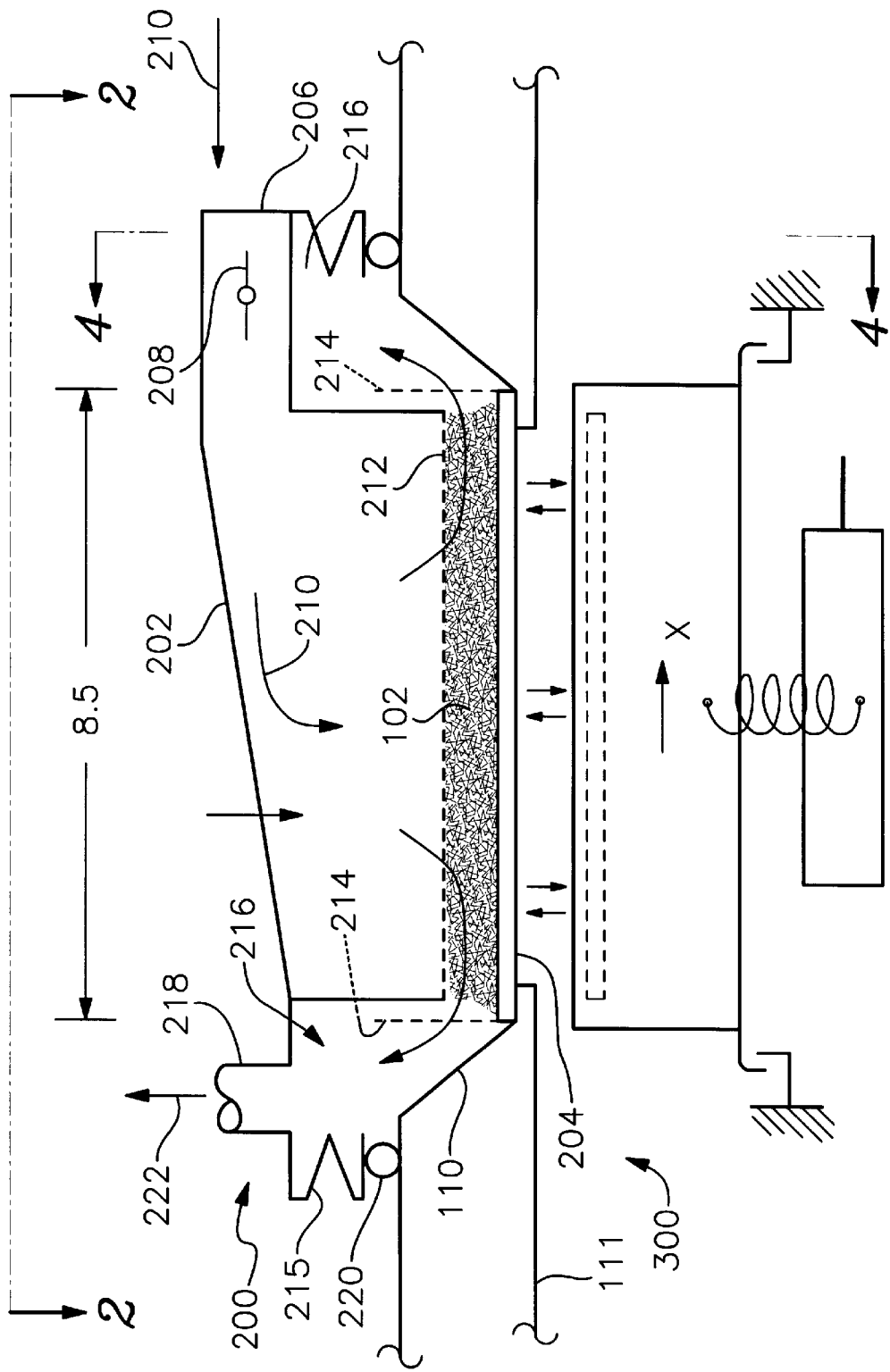
FIG. 3 is a side view of the Ultra-Rapid Conditioning module and the Color and Trash module.
Figure 4:
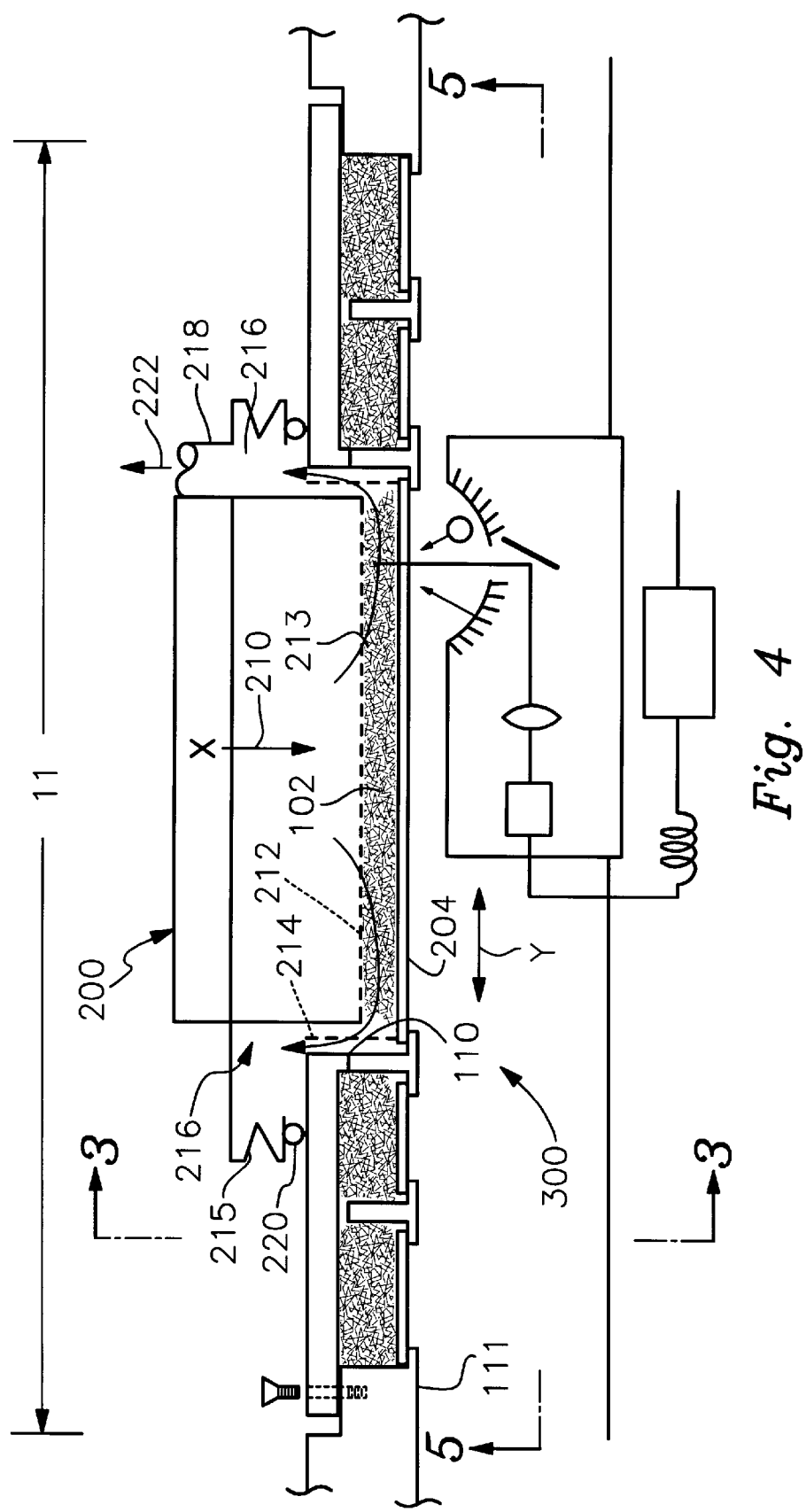
FIG. 4 is an end view of the Ultra-Rapid Conditioning module and the Color and Trash module.
Figure 5:
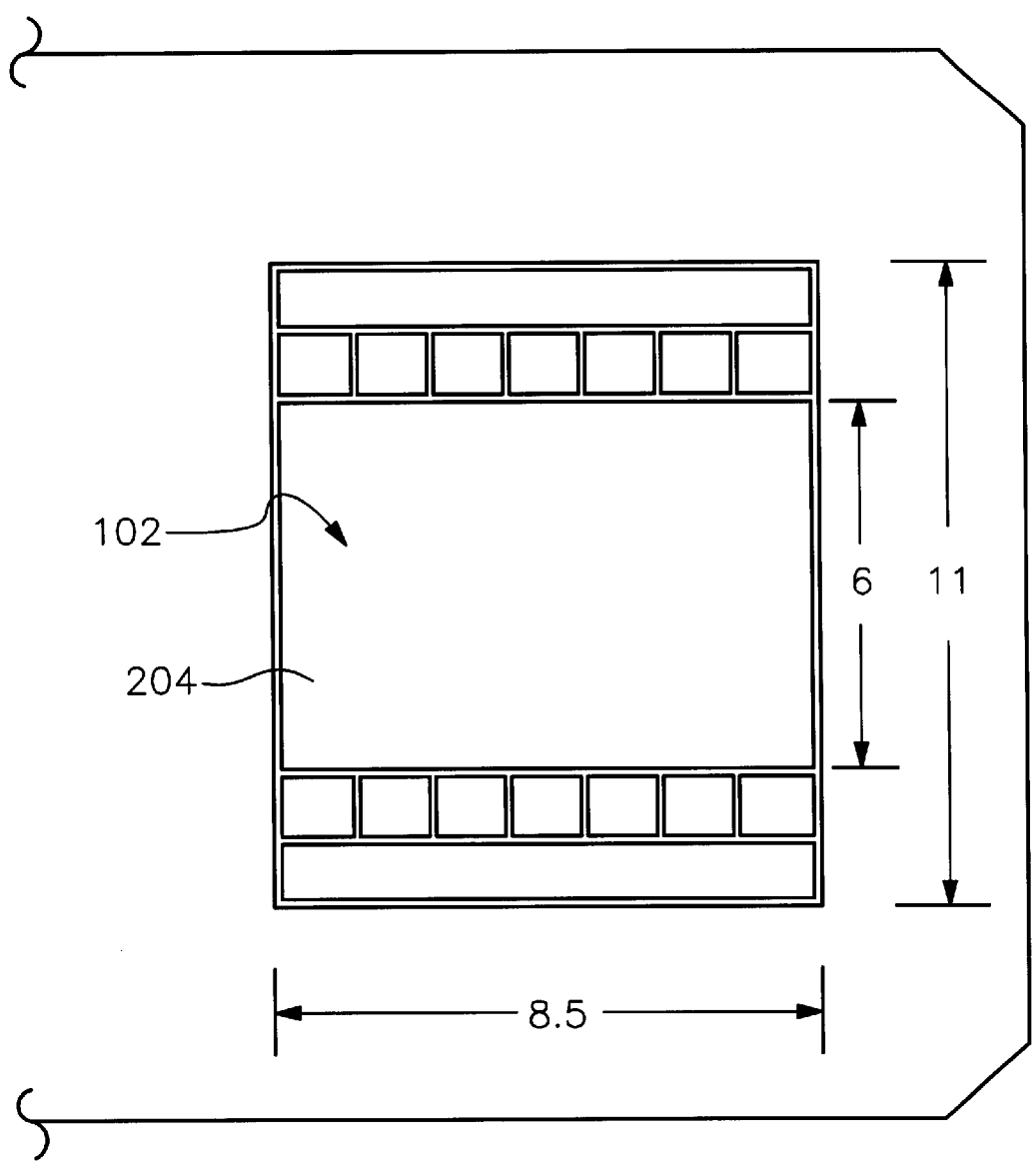
FIG. 5 is a bottom view of the Ultra-Rapid Conditioning module and the Color and Trash module, showing the optical imaging device field of view.

FIGS. 2–5 show both the Ultra-Rapid Conditioning module 200 and the Color and Trash module 300 of the instrument 100 of FIG. 1. FIG. 2 is a top view, without pressure/distribution cover plate 202; and FIG. 5 is a bottom view. The 8.5×8.5 inch (21.59×21.59 cm) area is a glass scanner window. FIGS. 3 and 4 are side and end views, respectively.

Conditioned gas flow 116 from module 114 in FIG. 1 is conducted towards the top of stable table 111, where typically: 120 CFM (3.4 m$^3$/min) of the 150 CFM (4.3 m$^3$/min) flow 116 is drawn into inlet 117 for transport and internal conditioning of belt 118, individualizer 120, and Micronaire-Maturity-Fineness module 400; approximately 20 CFM (0.6 m$^3$/min) flow 210 is drawn into the Ultra-Rapid Conditioning module 200; and the remainder is discharged to the production environment. Inlet 206 is in close proximity, but not tightly coupled, to inlet 117 to minimize egresses of conditioned gas or ingresses of unconditioned gas. Valve 208 is open for maximum conditioning flow and closed for applying pressure to sample 102 for the Color and Trash measurement. Valve 208 will be seen to be unnecessary in an alternative embodiment of pressure/distribution plate 202 described later in this section.

In a first alternative, conditioned (65% RH, 70° F. (21° C.)) gas flow 210 enters sample 102 via perforations in perforated plate 212. This flow 210 is constrained to move in the very narrow space, typically less than about 1 to 3 mm in thickness, between the perforated plate 212 and window 204 and exits via perforated plate sidewalls 214 into plenum 216, where it is drawn into conduit 218. If there are no leaks around seals 220 or elsewhere, the exiting flow 222 from plenum 216 is substantially equal to entering flow 210. Flows 210 and 222 will, of course, vary with the mass and other properties of sample 102.

The embodiments disclosed herein evolved from the "rapid conditioning" disclosed in Shofner et al Pat. No. 6,029,316. In that earlier disclosure, large, approximately, 100 to 300 gram, samples of cotton are "rapidly" conditioned. We have now discovered that thin, less than about 3 mm, low mass samples, within the approximate range 10 to 20 grams, will condition to proper moisture content for satisfactory testing or processing when actively ventilated in the intimately confined way, as disclosed above, in a matter of seconds, not the 14 to 60 minutes required of prior art "rapid conditioners," hence the designation "Ultra Rapid Conditioning." Extensions of prior art apparatus and methods fail to achieve the performance or the robust practicalities of the methods and apparatus recited here. We believe this failure to be in part explained by order of magnitude higher conditioning gas velocity through the fibers, of the order of 1000 ft/min (308 m/min) for Ultra-Rapid Conditioning versus 100 ft/min (31 m/min) for "rapid" conditioning. We also attribute some of the rapidity to the order of magnitude smaller sample size, 10 to 20 grams versus 100 to 300 grams. Contrariwise, if the design flow velocity of the instant, "ultra-rapid" conditioning invention were to be applied to the much larger sample mass of the prior "rapid" conditioning apparatus, the pressures and ventilation powers are absurdly excessive and/or the conditioning flow rate is ineffectively low.

By way of example, there are two alternative embodiments involving primarily valve 208 (FIG. 3) and perforated plate 212 (FIG. 3). Downward force on sample 102 in recessed conditioning/testing chamber 110 is important for the Color and Trash measurements.

In the first alternative for applying pressure to the sample 102 under test, valve 208 in FIG. 3 is open while conditioned air from module 114 is delivered to condition sample 102. In this first alternative, the holes in relatively thick and rigid perforated plate 212 are relatively large and the flow rate delivered for conditioning is high. After typically ten seconds, valve 208 partially closes and restricts flow 210 into Ultra-Rapid Conditioning module 200, thus causing a strong negative pressure or suction to be developed within pressure distribution plate 202. This suction causes atmospheric pressure to force plate 202 downward onto sample 102. Bellows 215 and seals 220 enable the downward movement and the suction, respectively. There is also an equal and opposite upward atmospheric pressure force on sample 102 exerted by window 204. Sample pressure is important for the Color and Trash measurement.

In the second, simpler alternative, there is no valve 208, and perforated plate 212 is preferably thinner and has fewer and/or smaller holes. These smaller holes in plate 212 inherently limit the flow 210 and thus develop the suction force across perforated plate 212, directly. Open areas of the order of 10% represent a satisfactory compromise between downward force, for Color and Trash measurements by module 300, and flow rate 210, for Ultra-Rapid Conditioning. This second alternative also enables parallel operations for Ultra-Rapid Conditioning processing by module 200 and for Color and Trash testing by module 300.

Figure 6:
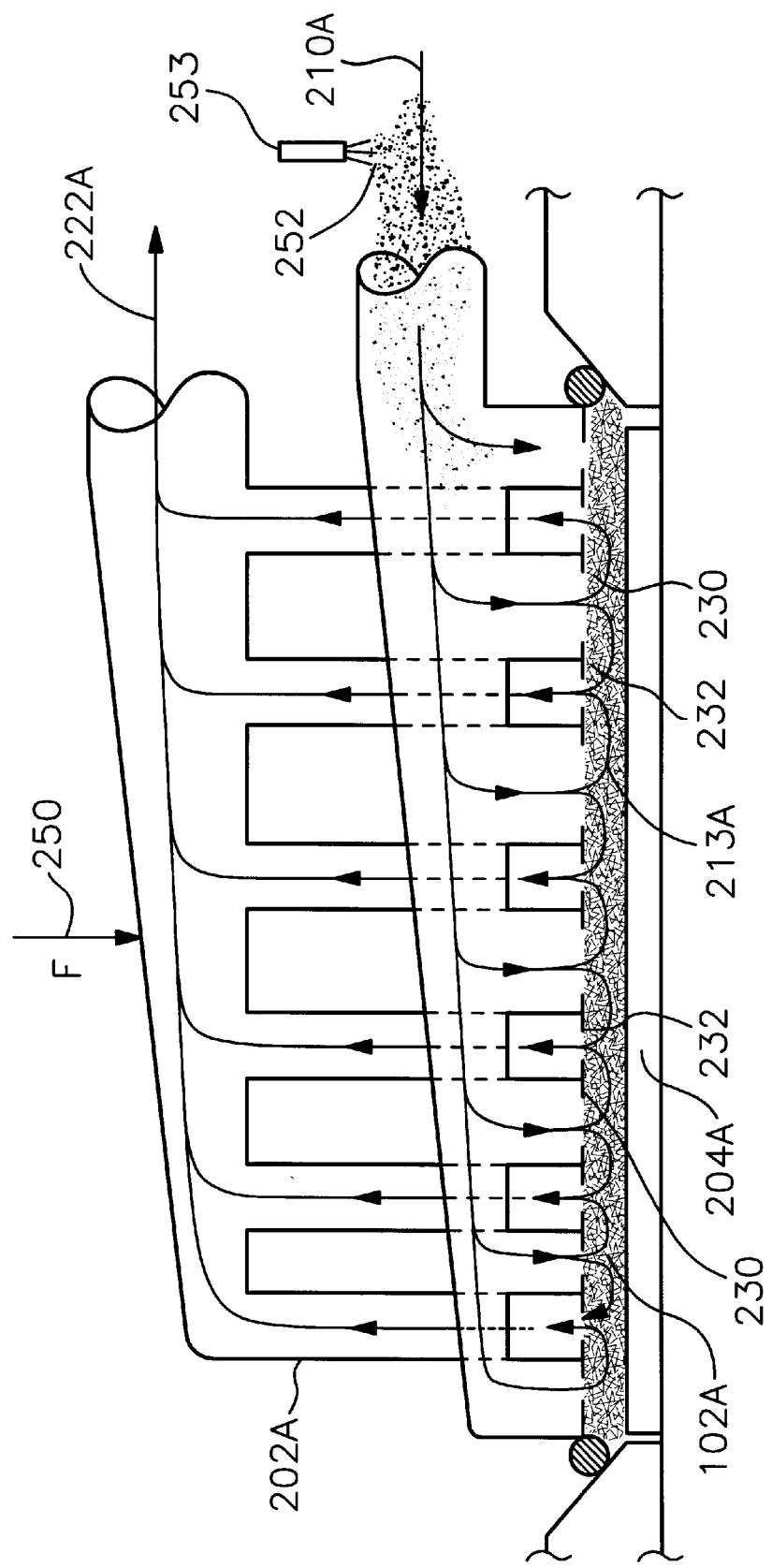
FIG. 6 shows an alternative pressure/distribution plate to that of FIG. 3, which achieves particularly short path lengths.

FIG. 6 shows a third alternative for pressurization and for flow delivery into and out of the sample 102a under test. A pressure/distribution plate 202a is employed for pressurization of sample 102a against window 204a and for delivery and distribution of conditioning flow into 210a and out of 222a the sample under test 102a. In FIG. 6, pressure/distribution plate 202a has a series of alternating passages 230 and 232 for respectively delivering gas flow to the cotton sample 102a and for allowing gas flow to exit from the cotton sample 102a. Thus entering gas flow 210a is driven through passages 230 into the cotton sample 102a, and gas flow exiting the cotton sample through passages 232 is combined as exiting gas flow 222a.

Pressure/distribution plate 202a operates in a manner similar to pressure/distribution plate 202 in performing the functions of Ultra-Rapid Conditioning Module 200. But there are significant differences. First, force F 250 is applied by mechanical means, as the differential pressures are developed internally and not available for pressurization as in FIG. 1. Second, the path lengths 213a from entry into and exit from sample 102a are much shorter than their corresponding lengths 213 in FIG. 1. These shorter paths enable much more intimate contact and higher flow rates, thus reducing conditioning times and improving uniformity. But, third and most importantly, the shorter path lengths 213a of pressure/distribution plate 202a enable delivery of aerosolized water 252 from an aerosolizer 253 uniformly. Explained next is why heretofore unknown uniform application of aerosolized water is important.

We discovered that the conditioning equilibration times for certain varieties of cotton, especially when they are very dry, below about 4% moisture content, require, when the samples are thick and the flow velocities are low, much more than the typical 15 minutes, as stated earlier. We also discovered, using operational parameters of the apparatus 200 in FIGS. 1, 2 and 3, that typical cottons will approach equilibrium in less than one minute. But the same difficult-to-condition varieties, when very dry, took several minutes to reach equilibria when the conditioning air had the ASTM standard conditions of 70° F. (21° C.) and 65% RH. Using the sample specific conditioning cycle procedures of Shofner et al U.S. Pat No. 6,029,316, in the apparatus 200 of FIGS. 1, 2 and 3, wherein, for example, the samples are initially exposed to 80% RH air for 30 seconds and then 65% air for 30 additional seconds, only allowed reaching equilibria in times approaching one minute.

As the speed of testing and processing is ever increasing, and even one minute is too long, it became clear that further improvements were essential and we discovered that deliveries of liquid water, in aerosolized form, to our thin mats, under proper conditioning can be effective. Delivery of liquid water to cotton fibers exploits the important and inherent feature of rapid and large absorbency. Whereas delivery of aerosolized water, sometimes containing chemicals to aid processing, has long been applied topically in cotton processing, it has been with mixed results. The difficulties relate to the unavoidable surface collection of aerosols by filtration effects. That is, applications of aerosolized water to a thick mat yield highly nonuniform collections that are primarily on the surface. Because cotton fibers, whose diameters are about 20 micrometers, quite effectively capture, by impaction, aerosols whose diameters are tens of micrometers, it follows that very short path lengths through the mats are essential.

Returning to FIG. 6, it may now be appreciated that the short path lengths 213a, which may be as short as 1 mm or less, enable uniform delivery of aerosolized water 252 throughout sample 102a or to corresponding process mat, as explained below. Said water may contain chemicals for processing aids as desired. Note that the inlet 210a and exit 222a flows may be reversed to improve uniformity of deliveries. Note also that the path lengths 213 in FIG. 1 are much longer, of the order of 100 mm. Whereas the apparatus of FIG. 1 is satisfactory when conditioning without aerosolized water delivery, the short paths 213a of FIG. 6 are required when aerosols are used.

The total water content, in grams/m$^3$, the balance of gaseous and liquid water, and aerosol 252 particle size distribution, at impaction or initial interaction with the mat, are key parameters. For the fastest deliveries and equilibrations, for testing purposes, the total water content can be equal to gaseous content without aerosols, ie, 65%, the aerosol component should be larger than the gaseous component, and the volume mean diameter and geometric standard deviation of the aerosol size distribution should be about 15 micrometers and 2.0, respectively. For processing purposes, the total water content is typically much higher, as the conditioning objectives are different. Indeed, total water content can exceed 100% or supersaturation.

Thus uniformly delivered, conditioning and equilibria times for testing and processing take on new possibilities and meanings. Subsecond equilibrations, and delivery times approaching milliseconds, are possible employing embodiments of the invention. Additionally, the importance of uniform deliveries, as accomplished with pressure/distribution plate 202a in FIG. 6, cannot be overemphasized.

Figure 7:
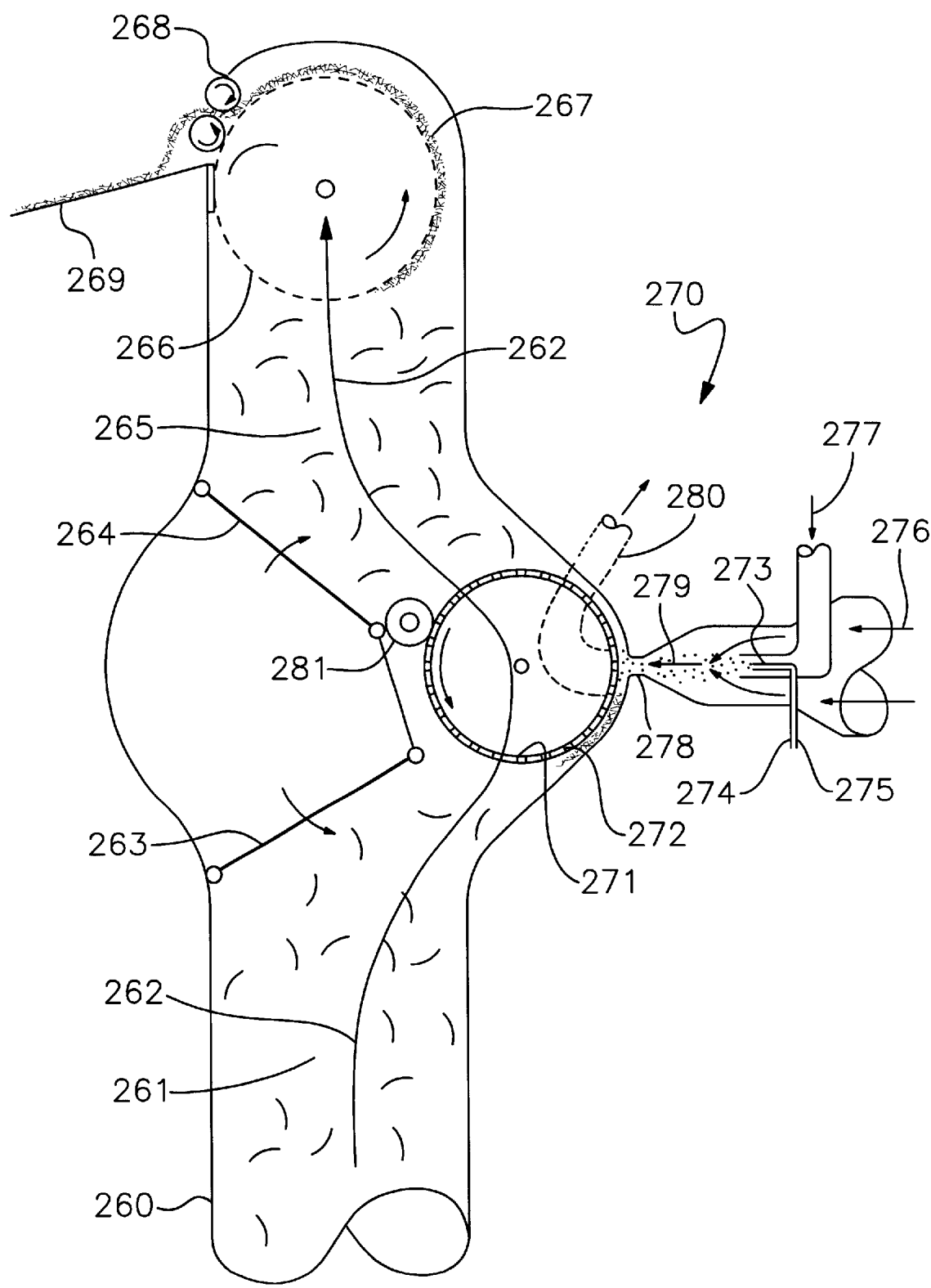
FIG. 7 shows a machine for conditioning cotton fiber in a processing environment, in particular, a cotton gin.

An important and representative processing embodiment 270 of the invention is seen in FIG. 7 and as applied to delivery of moisture, particularly aerosolized water, to the lint flue riser 260 of a cotton gin. Lint or cotton fibers 261, after ginning and cleaning, are pneumatically transported by air flow 262 which may be 50,000 CFM in a large gin producing one 500 pound bale per minute. Riser 260 is typically about 20 square feet (1.9 m$^2$) in area and usually rectangular in cross section.

Consider first operation without moistening station 270, which occurs if diverter panels 263,264 are rotated counterclockwise and clockwise, respectively, thus bypassing moistening station 270. Fibers and air are separated at the battery condenser 266, with the fibers captured on the exterior and forming a thick mat 267 and the air drawn out axially by a powerful fan. The mat 267 is stripped from condenser 266 by stripper rolls 268 and delivered to lint slide 269, after which it is baled. For reference, it is known to introduce sprayed aerosols onto mat 267 while it is on condenser 266 or lint slide 269, with the mixed results mentioned above because of the nonuniformities associated with surface capture. The mat 267 on condenser 266 may be 4 inches (100 mm) thick. It is also known to apply live steam or very high relative humidity air to the mat on the lint slide, also with mixed results, and for the reasons described above, wherein we found it difficult to rapidly equilibrate cotton samples even with very high relative humidity air.

When moistening station 270 is in operation, diverter panels 263 and 264 are in the positions shown in FIG. 7, and the fibers 261 and transport air 262 are diverted to high speed condenser 271, where a thin mat 272 is formed. Transport air 262 moves through condenser 271 and at the exit is also designated 262. The pressure drop introduced by the moistening station 270 is overcome by increased suction with the battery condenser 266 fan.

High speed condenser 271 is preferably constructed of perforated stainless steel, with perforation holes about 1 mm in diameter and with about 25% open area, and may be 36 inches (91.44 cm) in diameter, 72 inches (1.83 cm) long, and rotating at a speed of 1200 RPM. The mat 272 thus formed on high speed condenser 271 is indeed thin, less than about 1 mm. Stripper rolls 281 ensure the removal of conditioned fiber 265 from the e condenser 271, to be conveyed on to the battery condenser 266.

It is illustrative to calculate the surface density as an alternative confirmation of thinness:

$$\overline{W} = 500 \text{ pounds/minute } 1200 \, \pi \times 3 \times 6 \text{ square feet/minute} = 7.37 \times 10^{-3}$$
$$\text{pounds/square foot} = 23 \text{ mg/in}^2 \text{ (3.6 mg/cm}^2\text{)}$$

This average density corresponds to about 5 monolayers of fiber. It will be appreciated that this is thinner than the test sample path 213a in FIG. 6. It will also be appreciated that the illustrative dimensions and operating parameters may be modified to accommodate specific cotton gin or cotton mill applications without departing from the invention.

Aerosolized water is generated, for example by one or more two-fluid atomizer nozzles 273, with air 274 and water 275, with or without chemicals, delivered to the one or more of such nozzles to produce aerosolized water 278 at the rate and having the size distribution described above. The aerosols are introduced into and transported by sheath gas flow 277 and primary transport flow 276. Again, what matters are the aerosol and gaseous parameters 278 as delivered at the thin mat, also as described above, as evaporation can significantly alter these parameters. Sheath 277 and primary 276 gas flows combine as delivery flow 279 whose high velocity impacts the aerosols onto the fibers in the thin mat. An impaction flow velocity of about 5000 feet/min and volumetric flow rate of about 6000 CFM are appropriate for the ginning rate of one bale/hour used here for the example. Impaction flow 279 is driven by suction means (not shown) connected to conduit 280 which draws said impaction flow 279 through the perforations of the high speed moistening condenser cylinder 271.

The rate of aerosol delivery, which depends on the ginning rate and on the initial moisture content of the thin mat, is controlled through the driving air 274 or water supplied 275 in response to sensors and employing computers (not shown). If fibers are not present, most of the aerosol moves through the openings in the perforated condenser 271, so delivery of aerosols to the fiber is in part self-controlling.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A machine for conditioning cotton fiber being pneumatically transported by a gas flow, said machine comprising:
   a condenser in the form of a rotating perforated cylinder with inward gas flow such that fibers being transported are collected on said condenser as a thin mat;
   an aerosolizer for introducing aerosolized water for delivery to the thin mat; and
   means for re-delivering fibers from the thin mat on said high speed condenser to the transport gas flow.

2. The machine of claim 1, wherein at least one chemical is included in the aerosolized water.

3. The machine of claim 2, which further comprises means for controlling chemical concentration based on the rate fiber is transported.

4. The machine of claim 2, which further comprises means for controlling chemical composition based on the rate fiber is transported.

5. The machine of claim 1, which further comprises means for controlling the rate of aerosol delivery based on the rate fiber is transported and on the initial moisture content of the thin mat.

6. The machine of claim 1, which further comprises means for controlling the aerosol driving gas flow rate or the water supplied to said aerosolizer based on the rate fiber is transported and on the initial moisture content of the thin mat.

7. The machine of claim 1, which further comprises means for controlling the aerosol size distribution based on the rate fiber is transported and on the initial moisture content of the thin mat.

8. The machine of claim 1, which further comprises means for controlling aerosol impaction flow velocity based on the rate fiber is transported and on the initial moisture content of the thin mat.

9. The machine of claim 1, wherein said high speed condenser rotates at 1200 RPM.

10. A machine for conditioning cotton fiber being pneumatically transported by a gas flow, said machine comprising:

a condenser in the form of a rotating perforated cylinder with inward gas flow such that fibers being transported are collected on said condenser as a thin mat less than about 1 mm in thickness;

an aerosolizer for introducing aerosolized water for delivery to the thin mat.

11. The machine of claim 10, wherein said thin mat is about 5 monolayers in thickness.

12. The machine of claim 10, wherein said thin mat has a surface density of approximately 23 mg/in$^2$ (3.6 mg/cm$^2$).

13. A machine for conditioning cotton fiber being pneumatically transported by a gas flow, said machine comprising:

a perforated surface on which fibers being transported are collected as a thin mat;

an aerosolizer for introducing aerosolized liquid for delivery to the thin mat; and means for re-delivering fibers from the thin mat on said perforated surface to the transport gas flow.

14. The machine of claim 13, wherein said aerosolizer introduces aerosolized water.

15. The machine of claim 14, wherein at least one chemical is included in the aerosolized water.

16. The machine of claim 15, which further comprises means for controlling chemical concentration based on the rate fiber is transported.

17. The machine of claim 15, which further comprises means for controlling chemical composition based on the rate fiber is transported.

18. The machine of claim 13, which further comprises means for controlling the rate of aerosol delivery based on the rate fiber is transported and on the initial moisture content of the thin mat.

19. The machine of claim 13, which further comprises means for controlling the aerosol driving gas flow rate or the water supplied to said aerosolizer based on the rate fiber is transported and on the initial moisture content of the thin mat.

20. The machine of claim 13, which further comprises means for controlling the aerosol size distribution based on the rate fiber is transported and on the initial moisture content of the thin mat.

21. The machine of claim 13, which further comprises means for controlling aerosol impaction flow velocity based on the rate fiber is transported and on the initial moisture content of the thin mat.

22. A machine for conditioning cotton fiber being pneumatically transported by a gas flow, said machine comprising:

a perforated surface on which fibers being transported are collected as a thin mat less than about 1 mm in thickness;

an aerosolizer for introducing aerosolized liquid for delivery to the thin mat.

23. The machine of claim 22, wherein said thin mat is about 5 monolayers in thickness.

24. The machine of claim 22, wherein said thin mat has a surface density of approximately 23 mg/in$^2$ (3.6 mg/cm$^2$).

25. A method for conditioning cotton fiber being pneumatically transported by a gas flow, said method comprising:

collecting fibers to form a thin mat;

delivering aerosolized liquid to the thin mat; and re-delivering conditioned fiber from the thin mat into the gas flow.

26. The method of claim 25, which comprises collecting fibers to form a mat less than, about 1 mm in thickness.

27. The method of claim 25, which comprises collecting fibers to form a mat having a thickness of about 5 monolayers.

28. The method of claim 25, which comprises collecting fibers to form a mat having a surface density of approximately 23 mg/in$^2$ (3.6 mg/cm$^2$).

29. The method of claim 25, wherein said step of collecting fibers to form a thin mat comprises collecting fibers on a perforated surface with gas flow through perforations.

30. The method claim 29, wherein said step of collecting fibers to form a thin mat comprises collecting fibers on a rotating perforated cylinder that has inward gas flow.

31. The method of claim 25, wherein said step of delivering aerosolized liquid to the thin mat comprises delivering aerosolized water to the thin mat.

32. The method of claim 31, wherein at least one chemical is included in the aerosolized water.

33. The method of claim 32, which further comprises controlling chemical concentration based on the rate fiber is transported.

34. The method of claim 32, which further comprises controlling chemical composition based on the rate fiber is transported.

35. The method of claim 25, which further comprises controlling the rate of aerosol delivery based on the rate fiber is transported and on the initial moisture content of the thin mat.

36. The method of claim 25, which further comprises controlling aerosol driving gas flow rate or the water supplied to an aerosolizer based on the rate fiber is transported and on the initial moisture content of the thin mat.

37. The method of claim 25, which further comprises controlling aerosol size distribution based on the rate fiber is transported and on the initial moisture content of the thin mat.

38. The method of claim 25, which further comprises controlling the aerosol impaction flow velocity based on the rate fiber is transported and on the initial moisture content of the thin mat.

* * * * *